United States Patent [19]

Sponer et al.

[11] Patent Number: 5,026,706

[45] Date of Patent: Jun. 25, 1991

[54] METHOD FOR TREATING DYSURIA USING NAFTOPIDIL

[75] Inventors: Gisbert Sponer, Laudenbach; Ulrich Reicke, Hirschberg-Leutershusen; Michael Nelboeck-Hochstetter, Tutzing, all of Fed. Rep. of Germany

[73] Assignee: Boehringer Mannheim GmbH, Mannheim, Fed. Rep. of Germany

[21] Appl. No.: 530,362

[22] Filed: May 30, 1990

[30] Foreign Application Priority Data

Jun. 7, 1989 [DE] Fed. Rep. of Germany ....... 3918543

[51] Int. Cl.$^5$ ............................................. A61K 31/495
[52] U.S. Cl. .................................................... 514/255
[58] Field of Search ......................................... 514/255

*Primary Examiner*—Stanley J. Friedman
*Attorney, Agent, or Firm*—Armstrong, Nikaido, Marmelstein, Kubovcik & Murray

[57] ABSTRACT

Naftopidil,1-(2-methoxyphenyl)-4-[3-(naphth-1-yloxy)-2-hydroxypropyl)]-piperazine, or of a salt thereof, is effective in the treatment of dysuria, particularly in causes of prostatic hypertrophy.

4 Claims, No Drawings

METHOD FOR TREATING DYSURIA USING NAFTOPIDIL

The present invention is concerned with the use of naftopidil for the therapy of dysuria, particularly in cases of benign prostatic hypertrophy.

Naftopidil, the chemical name of which is 1-(2-methoxyphenyl)-4-[3-(naphth-1-yloxy)-2-hydroxypropyl]-piperazine, is described in U.S. Pat. No. 3,997,666 as being a compound with outstanding blood pressure lowering and thus antihypertensive properties. Furthermore, it is said to inhibit the anaphylactoid reactions in rats induced by dextran.

In the case of clinical investigations with naftopidil, we have now found that the compound alleviates complaints of dysuria, particularly in cases of prostatic hypertrophy. The complaints are characterized by a disturbance in micturition, especially the urge to micturate during the night. As a rule, this affects men over 60 years. Hitherto, a specific therapy has not been established. By way of experiment, use has been made of active materials based on plant extracts or on $\beta$-sitosterol.

The effectiveness of naftopidil for the treatment of dysuria due to prostatic hypertrophy has been demonstrated by the clinical study described in detail below.

The investigations were carried out on a total of 39 patients. 37 of the patients suffered from prostatic hypertrophy. After a preliminary period of one week in which placebo medication was administered, naftopidil was administered in doses of from 12.5 to 100 mg. daily. The dose administered depended upon the effectiveness: in the case of insufficient action, the dose was doubled at intervals of one week, commencing with 12.5 mg.

As criteria, inter alia, there were chosen: frequency of micturition during the day and during the night, period of time of micturition, urine flow, abdominal pressure in order to be able to micturate, as well as sensation during micturition.

The evaluation took place on the basis of a scale with the following classification: distinctly improved, improved, slightly improved, unchanged, worsened.

A total of 34 patients could be included in the evaluation. Of these, 8 were distinctly improved, 14 improved, 7 slightly improved, 1 patient had a unchanged retention and, in the case of 4 further patients, no distinct decision could be made.

For the preparation of pharmaceutical compositions, naftopidil, or a pharmaceutically acceptable salt thereof, is mixed in known manner with appropriate pharmaceutical carrier substances, aroma, flavoring and coloring materials and formed, for example, into tablets or dragees or, with the addition of appropriate adjuvants, suspended or dissolved in water or in an oil, for example olive oil. The preparation of naftopidil, and its salts, is described in the aforesaid U.S. Pat. No. 3,997,666, the disclosure of which is incorporated herein by reference.

Naftopidil is usually administered, preferably orally, in amounts of from 10 to 100 mg. per day. It is preferred to administer it once or twice a day in individual doses of 10 to 50 mg.

A example of a formulation for a tablet containing 25.0 mg. of active material has the following composition:

| | |
|---|---|
| naftopidil | 25.0 mg. |
| lactose monohydrate | 110.0 mg. |
| poly-(1-vinyl-2-pyrrolidone) (M.W. 25,000) | 3.0 mg. |
| microcrystalline cellulose | 15.0 mg. |
| highly dispersed silicon dioxide | 1.5 mg. |
| poly-(O-carboxymethyl)-starch, sodium salt | 4.0 mg. |
| magnesium stearate | 1.5 mg. |
| | 160.0 mg. |

What is claimed is:

1. A method for treating the dysuria in a patient afflicted with dysuria, which comprises orally administering to the patient an amount of naftopidil, or a pharmaceutically acceptable salt thereof, sufficient to improve micturation.

2. A method according to claim 1, wherein the naftopidil is administered once or twice a day.

3. A method according to claim 2, wherein 10 to 100 mg. of naftopidil is administered per day.

4. A method according to claim 1, wherein the patient has benigh prostatic hypertrophy.

* * * * *